(12) United States Patent
Szell et al.

(10) Patent No.: US 6,506,591 B2
(45) Date of Patent: Jan. 14, 2003

(54) PROCESS FOR THE PREPARATION OF PSEUDOMONIC ACID A ANTIBIOTIC BY MICROBIOLOGICAL METHOD

(75) Inventors: Valeria Szell, Budapest (HU); Ildiko Lang, Budapest (HU); Istvan Barta, Buapest (HU); Aniko Tedges, Budapest (HU); Karoly Albrecht, Budapest (HU); Julianna Mozes Nee Suto, Budapest (HU); Istvan M. Szabo, Budapest (HU); Magdolna Petroczki, Budapest (HU); Janos Erdei, Debrecen (HU); Eva Gulyas, Debrecen (HU); Gabor Balogh, Debrecen (HU)

(73) Assignee: Biogal Gyogyszergyar Rt., Debrecen (HU)

( * ) Notice: Subject to any disclaimer, the term of this patent is extended or adjusted under 35 U.S.C. 154(b) by 0 days.

(21) Appl. No.: 09/975,796

(22) Filed: Oct. 11, 2001

(65) Prior Publication Data

US 2002/0042103 A1 Apr. 11, 2002

Related U.S. Application Data

(62) Division of application No. 09/497,807, filed on Feb. 3, 2000.
(60) Provisional application No. 60/118,457, filed on Feb. 3, 1999, and provisional application No. 60/137,334, filed on Jun. 3, 1999.

(51) Int. Cl.[7] ................................................. C12N 1/20
(52) U.S. Cl. ..................... 435/253.3; 435/125
(58) Field of Search .............................. 435/253.3, 123, 435/125

(56) References Cited

U.S. PATENT DOCUMENTS 3,977,943 A    8/1976  Barrow et al.
4,071,536 A    1/1978  Barrow et al.

FOREIGN PATENT DOCUMENTS

JP            52070083    *    6/1977

OTHER PUBLICATIONS

Mantle, et al., FEMS Microbiol. Lett. (1989), 59(1–2), 55–8.*
Feline, et al., J. Chem. Soc., Perkin Trans. 1 (1977), (3), 309–18.*

Feline et al. "Pseudomonic acid. Part 2. Biosynthesis of pseuomonic acid A." Journal Chemical Society, Perkin Trans. I. 1977, pp. 309–318.

Mantle et al. "Radiolabelling of the monate moiety in the study of pseudomonic acid biosynthesis," FEMS Microbiol. Lett. 1989, vol. 59, No. 12, pp. 55–58.

Martin et al. "Biosynthetic studies on pseudomonic acid (mupirocin), a novel antibiotic metabolite of Pseudomonas fluorescenes," Journal Chemical Society Perkin Trans. I. 1989, pp. 207–209.

Ward et al. "Mupirocin—A review of Its Antibacterial Activity, Pharmacokinetic Properties and Therapeutic Use," Drugs. 1986, vol. 32, No. 5, pp. 382–475.

Hughes et al. "Interaction of pseudomonic acid A with *Escherichia coli* B isoleucyl–tRNA synthetase." Biochemical Journal. 1980, vol. 191, pp. 209–219.

Chain et al. "Structure of Pseudomonic Acid, an Antibiotic from *Pseudomonas fluorescens*."Journal of the Chemical Society, Chemical Communications. Jan. 1974, No. 1, pp. 847–848.

Alexander et al. "The Chemistry of Pseudomic Acid. Part 1. The Absolute Configuration of Pseudomonic Acid A." Journal of the Chemical Society, Perkin Transactions I, Organic and Bio–organic Chemistry. 1978, pp. 561–565.

Palleroni. "Psuedomonaceae." Bergey's Manual of Systematic Bacteriology. 1984, vol. 1, pp. 141–219.

* cited by examiner

*Primary Examiner*—Irene Marx
(74) *Attorney, Agent, or Firm*—Kenyon & Kenyon

(57) ABSTRACT

A procedure for the preparation of pseudomonic acid A comprising submerged cultivation of a Pseudomonas bacterium strain capable of biosynthesis of the substantially pure pseudomonic acid A in aerated conditions via fermentation; and isolation of the desired compound is disclosed. In particular, the procedure of the present invention comprises cultivation of the Pseudomonas sp. bacterium strain No. 19/26 deposited under accession No. NCAIM(P)B 001235 in the National Collection of the Agricultural and Industrial Microorganisms, Budapest, Hungary, or its pseudomonic acid A-producing mutant or variant, on a medium at a temperature of between about 20° C. and 30° C. containing organic nitrogen and carbon sources and, optionally, mineral salts.

1 Claim, 1 Drawing Sheet

PROCESS FOR THE PREPARATION OF PSEUDOMONIC ACID A ANTIBIOTIC BY MICROBIOLOGICAL METHOD

CROSS REFERENCE TO RELATED APPLICATION

This application is a division of U.S. Ser. No. 09/497,807, filed Feb. 3, 2000 which claims benefit of Provisional Applns No. 60/118,457 filed Feb. 3, 1999 and No. 60/137,334 filed Jun. 3, 1999.

FIELD OF THE INVENTION

The present invention relates to a microbiological method for the manufacture of the antibiotic pseudomonic acid A (mupirocin).

BACKGROUND OF THE INVENTION

Pseudomonic acid A, also known as mupirocin, is an antibiotic that has a growth inhibiting effect mainly against Gram positive bacteria (e.g. *Staphylococcus aureus, Streptococcus pyogenes, Streptococcus pneumoniae, Klebsiella pneumoniae*) and some Gram negative bacteria (e.g. *Haemophilus influenzae, Neisseria gonorrhoeae*) [A. Ward, D. M. Campoli-Richards, Drugs 32, 425–444 (1986)] and its minimal inhibiting concentration is in the range of 0.02–0.5 mg/dm$^3$. Pseudomonic acid A, by inhibiting the isoleucine-tRNA synthase enzyme, affects the peptide synthesis of pathogen bacteria [J. Hughes and G. Mellows, Biochem. J. 191, 209–219 (1980)]. An advantageous feature of this antibiotic is that it has very low toxicity both for humans and animals and it is negative in the Ames test. Pseudomonic acid A is presently used in human therapy, in various formulations, for the treatment of skin infections (e.g. impetigo, pyoderma), nose and external ear infections, acne, burns, eczema, psoriasis, in case of ulceration for treatment of secondary infections, and for prevention of hospital infections.

The chemical structure of pseudomonic acid A was determined to be 9-{4[5S(2S,3S-epoxy-5S-hydroxy-4S-methylhexyl)-3R,4R-dihydroxy-tetrahydropyran-2S-yl]-3-methylbut-2(E)-enoyloxy}nonanoic acid [E. B. Chain and G. Mellows, J. C. S. Chem. Comm. 847–848 (1974); R. G. Alexander, J. P. Clayton, K. Luk, N. H. Rogers, T. J. King, J. C. S. Perkin I. 561–565 (1978)], as depicted by formula (I):

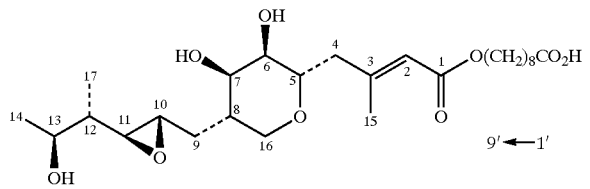

(I)

It is known that *Pseudomonas fluorescens* is able to produce the pseudomonic acid A. According to the British Patent No. 1,395,907, the *Pseudomonas fluorescens* NCIB 10586 strain is able to biosynthesize the pseudomonic acid complex consisting of pseudomonic acid A and its isomer being a double bond in the cis position between the carbon atoms C$_2$ and C$_3$ and pseudomonic acid B. The ratio of the components is 4.5:4.5:1. According to the Japanese patent application No. 52-70083, however, the *Pseudomonas fluorescens* Y-11633 strain is able to biosynthesize the pseudomonic acid complex consisting of the pseudomonic acid A, pseudomonic acid B and further two components with unknown structures in the ratio of 9:0.5:0.5.

SUMMARY OF THE INVENTION

The present invention is directed to a procedure for the preparation of pseudomonic acid A comprising cultivating on a medium comprising at least one organic nitrogen or carbon source, in submerged aerated conditions, a Pseudomonas bacterium strain capable of the biosynthesis of pseudomonic acid A, and fermentation of the Pseudomonas culture such that pseudomonic acid A is formed. Preferably the Pseudomonas bacterium strain is Pseudomonas sp. bacterium strain No. 19/26 deposited under accession No. NCAIM(P)B 001235 in the National Collection of Agricultural and Industrial Microorganisms, Budapest, Hungary, or its pseudomonic acid A-producing mutant or variant.

The present invention also is directed to a Pseudomonas culture capable of biosynthesizing pseudomonic acid A in submerged aerated conditions, consisting essentially of a novel Pseudomonas sp. bacterium strain No. 19/26.

The present invention further is directed to a biologically pure culture of a novel Pseudomonas sp. bacterium strain No. 19/26.

DETAILED DESCRIPTION OF THE INVENTION

Figure 1:
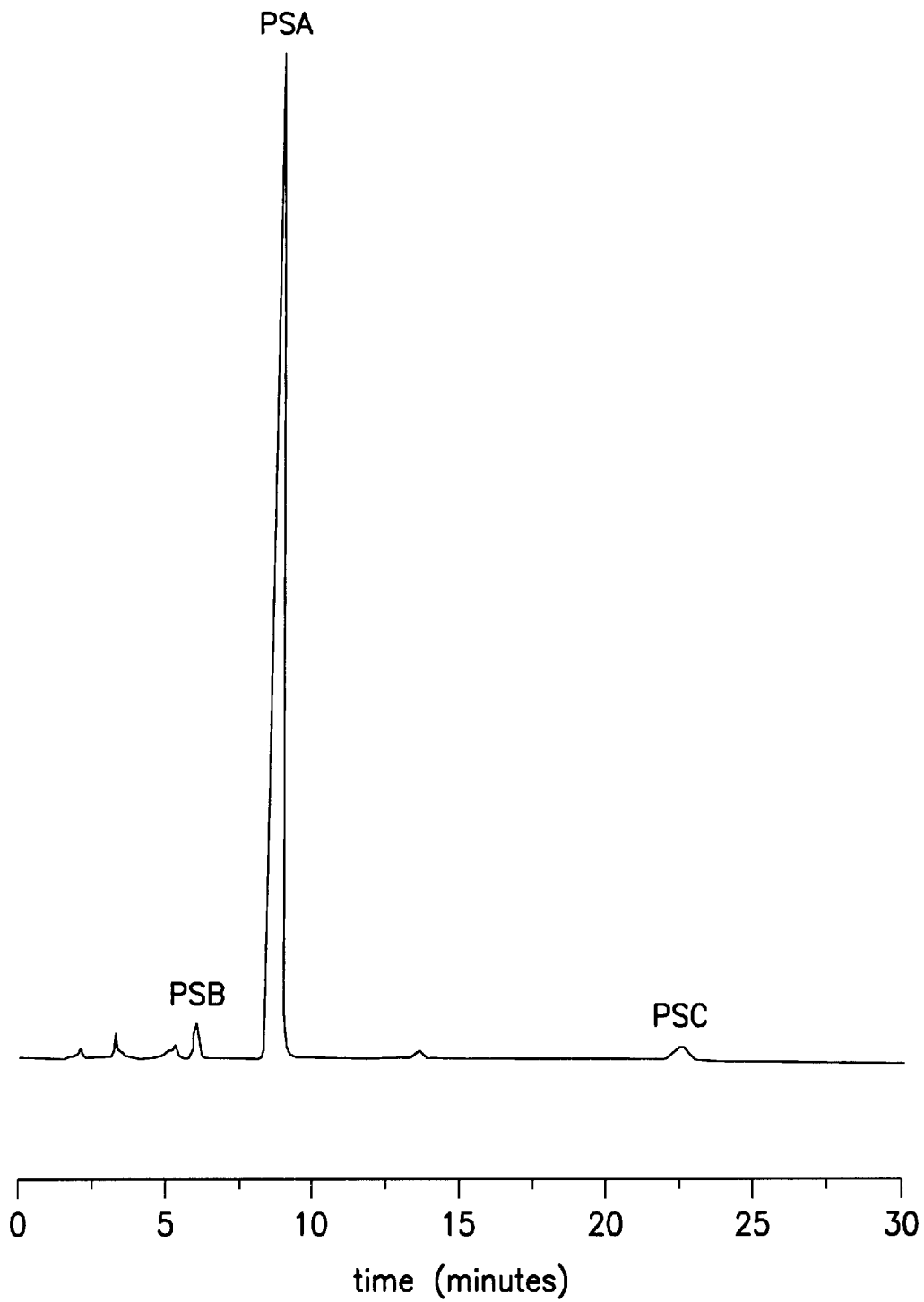
FIG. 1 is an HPLC chromatogram of the pseudomonic acid complex produced by Pseudomonas sp. No. 19/26 [NCAIM(P)B 001235].

In the course of searching antimicrobial antibiotics produced by bacteria, 20,000 microorganisms were isolated on nutrient agar medium containing 10 μg/ml candicin and 5 μg/ml cycloheximide in order to prevent the growth of fungi.

Antibacterial effectiveness of the shaken flask culture of the isolated bacterial strains was examined on different Gram positive and Gram negative test-microorganisms and their resistant variants for antibiotics occurring in the therapeutic practice. By the application of the antibiotic resistant test-microorganisms we wanted to promote the recognition of antibacterial antibiotics with new mode of action.

In the course of the above described examinations a bacterium isolate, designated as "strain No. 19/26," was selected. Originally, this organism had been obtained from a soil sample collected in Argentina. Its culture broth had significant antibiotic effect against *Bacillus subtilis* ATCC 6633, *Staphylococcus aureus* SMITH, the penicillin-resistant *Staphylococcus aureus* 1110, an unnumbered *Streptococcus pneumoniae* strain, *Streptococcus pyogenes* A 115 ROBB, *Alcaligenes faecalis* 140001, *Bordetella bronchiseptica* ATCC 4617, *Klebsiella pneumoniae* ATCC 10031, the meticillin- and aminoglucoside-resistant *Staphylococcus aureus* MRSA 119OR and two unnumbered *Mycoplasma pneumoniae* and *Haemophilus influenzae* strains, respectively. Later the antibacterial metabolic product of strain No. 19/26 was isolated from its culture broth and as a result of a chemical structure analysis it was found to be identical to the pseudomonic acid A.

At the same time this selected pseudomonic acid A-producing bacterium strain was subjected to taxonomic studies. First a preliminary comparative investigation was done with selected closely related bacterial strains using the Bio-Merieux ATB Expression equipment with ID 32 GN strip. The latter is suitable for a relatively fast (e.g. generic level) taxonomic identification of a given unknown bacterial strain if its diagnostic properties can show a desired high degree of phenetic similarity to at least one of those of the authentic strains that were incorporated in the database of the equipment. Carbon-source utilization spectra of an unknown bacterial strain to be investigated can be determined with this equipment in 32 tests with 14 different sugars and 14 organic acids, respectively, added into a minimal culture medium completed with a complex of growth factors. Evaluation of the utilization test results is done after the inoculation and passing 48 hours incubation time by means of automatic turbidity measurement on the developed microcultures designating the growth intensities (the reactions) as + or − or ?, respectively. The results of the synchronously studied biochemical tests are evaluated by the software of the equipment. The obtained physiological-biochemical data of strain No. 19/26 were correlated with those of the bacterial strains that are listed in the database (the total number of such strains is in this case 114, among them 14 belonging to different Pseudomonas species: *Pseudomonas aeruginosa I* and *II, Pseudomonas alcaligenes, Pseudomonas fluorescens I* and *II, Pseudomonas mendocina, Pseudomonas mesophilica, Pseudomonas pickettii, Pseudomonas pseudomallei, Pseudomonas vesicularis, Pseudomonas cepacia, Pseudomonas diminuta, Pseudomonas putida,* and *Pseudomonas stutzeri*). According to the outcome of this correlation experiment, strain No. 19/26 proved to be a member of the genus Pseudomonas.

After successful identification at generic level of strains No. 19/26 we tried to identify it at species level by means of classical taxonomic investigation method.

Cultures of strain No. 19/26 can multiply on suitable solid media in form of non-sporulating Gram negative rods, 0.6–1.1 to 1.3–4.0 microns. These are actively motile with polar flagella. These obligately aerobic chemoorganotrophic rods can attack glucose only oxidatively. They cannot ferment and are unable to respire with nitrates as terminal electron acceptors, but show positive catalase reaction. They do not develop visible colonies on simple synthetic media and for their multiplication always require growth factors. Growing under optimal conditions their colonies are argin-indihydrolase positive, produce fluorescent pigments but the presence and accumulation of poly-β-hydroxy-butyrate in the cells cannot be detected.

Further features of strain No. 19/26 are the following: development of its colonies was not observed at 41° C.; it does not produce levan from sucrose, it does not hydrolyze gelatin and starch, it is oxidase positive, and it does not utilize glucose, 2-keto-gluconate, trehalose and meso-inositol as the sole carbon source.

All of these diagnostic properties clearly separate the Pseudomonas strain No. 19/26 from the species *P. aeruginosa, P. fluorescens, P. chlororaphis, P. aureofaciens, P. syringae, P. viridiflava, P. cichorii, P. stutzeri, P. mendocina, P. alcaligenes, P. pseudoalcaligenes* and *P. putida* species. Cultivation of strain No. 19/26 can be carried out only on media prepared with (0.2–1.0%) yeast extracts, corn steep liquor or other complex natural nutrients containing very different growth factors.

On the basis of these particular diagnostic properties strain No. 19/26 can be considered as an organism which belongs to the so called "non-typical Pseudomonas species." Such "non-typical Pseudomonas species" may be incorporated into a newly established bacterial taxon in the future. (N. J. Palleroni, "Psuedomonaceae," Bergey's Manual of Systematic Bacteriology, 1,141–219, ed.: N. R. Krieg and J. G. Holt, Baltimore: Williams and Wilkins, 1984)

Strain No. 19/26 was deposited on Jul. 16, 1996 under accession No. NCAIM(P)B 001235 in the National Collection of Agricultural and Industrial Microorganisms, Budapest, Hungary.

According to a preferred method of the invention the Pseudomonas sp., bacterium strain No. 19/26 deposited under accession No. NCAIM(P)B 001235 is used for the manufacture of substantially pure pseudomonic acid A. The selected strain can use peptone, beef extract, corn steep liquor, yeast extract, casein and soy-bean meal as nitrogen sources. Besides the above nitrogen sources, carbon sources such as glucose, glycerol and sunflower oil can be applied in different combinations.

Although the medium components of natural origin contain mineral salts, it is advantageous to add some mineral salts (e.g. ammonium, calcium, iron, zinc, copper, magnesium, manganese, sodium or potassium salts) to the seed culture medium. Magnesium sulfate, manganese dichloride, ferrous sulfate, zinc chloride, copper II sulfate, ammonium sulfate, potassium dihydrogen phosphate, sodium chloride and calcium carbonate are preferred.

Maintenance of the strain is carried out on slant agar medium containing peptone-casein at 4° C., freshly transferring it every two weeks. To maintain the pseudomonic acid A productivity, the strain can be stored properly both by deep-freezing the culture or in lyophilized form.

In the course of the fermentation, the Pseudomonas sp. No. 19/26 strain is seeded into a suitable medium and cultivated in submerged and aerated fermentation conditions. The pH of the culture medium is preferably set to a neutral value (pH=about 7.0), the temperature of the cultivation between is about 20° C. and about 30° C., preferably between about 24° C. and about 26° C. Depending on the fermentation conditions the maximum value of the antibiotic productivity can be reached after 50–60 hours. The pseudomonic acid complex being formed in the course of the fermentation comprises substantially pure pseudomonic acid A, although as a result of the biosynthesis, small quantities of the pseudomonic acid B of formula (II)

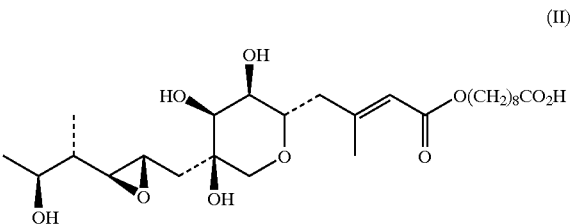

(II)

and pseudomonic acid C of formula (III)

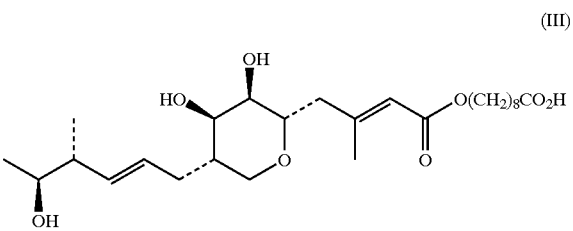

(III)

are also formed.

The antibacterial activity of the pseudomonic acid antibiotic complex is determined by agar diffusion microbial method. The medium is a beef-extract-peptone-glucose-containing agar, its pH is 6.5 and the test organism is

*Bacillus subtilis* ATCC 6633. The activity value obtained by the microbiological method represents primarily the quantity of the pseudomonic acid A, since the quantity of the other pseudomonic acid components is very small, and relating to the component A their specific activity against the test-microorganism—especially in the case of the component B—is considerably weaker.

In the course of the fermentation the exact quantity of the pseudomonic acid A and the accompanying minor components in the fermentation broth are determined by high pressure liquid chromatography (HPLC) in which the supernatant of the ultrasonic treated and centrifuged sample of the broth diluted to twice by ethanol is investigated (equipment: LKB 2248 pump, LKB 2141 UV detector (analysis at 222 nm), column: Nucleosil $C_8$ 10 μm (BST), eluent: mixture (35:65) of acetonitrile and 0.1 M $NH_4H_2PO_4$ solution (pH:5.0), flow rate: 1.2 ml/min), Retention times: pseudomonic acid A (PSA) is 8.5 min, pseudomonic acid B (PSB) is 6.0 min, and pseudomonic acid C (PSC) is 22.5 min.

The HPLC chromatogram of the pseudomonic acid antibiotic complex biosynthesized by Pseudomonas sp. No. 19/26 strain can be seen in FIG. 1. This chromatogram indicates that the pseudomonic acid complex obtained by the fermentation acid No. 19/26 strain of substantially pure pseudomonic acid A. The total quantity of the pseudomonic acid B and pseudomonic acid C components is below 5%. In this way it became evident that the Pseudomonas sp. No. 19/26 strain is able to biosynthesize the antibiotic in a more favorable composition, than the pseudomonic acid complex producing—*Pseudomonas fluorescens* strains published earlier. This fact is advantageous for industrial production.

The process according to the present invention is illustrated by the example below. However, the present invention should not be construed as limited thereby.

EXAMPLE

Pseudomonas sp. No. 19/26 strain was maintained on PCA marked slant agar medium. Composition of the PCA medium was the following:

| | |
|---|---|
| beef extract | 3 g |
| peptone | 5 g |
| agar | 15 g | diluted up to 1000 ml with distilled water. The pH of the medium was 7.0–7.2.

Seeded slant agar was incubated at 25° C. for 24 hours, and the cells were suspended in 5 ml normal saline solution (cell number in the suspension: $10^9$–$10^{10}$/ml). 1 ml of the suspension obtained was seeded into 100 ml I-21 marked seed culture medium sterilized in a 500 ml Erlenmeyer flask. Composition of I-21 medium was the following:

| | |
|---|---|
| glucose | 10 g |
| glycerol | 5 g |
| corn steep liquor | 3 g |
| ammonium sulfate | 2 g |
| potassium dihydrogen phosphate | 0.4 g |
| magnesium sulfate-water (1:7) | 0.4 g |
| manganese dichloride-water (1:2) | 0.03 g |
| calcium carbonate | 4 g |
| sunflower oil | 2 g | diluted up to 1000 ml with tap water. The pH of the medium is set to 7.0 before sterilization.

The flask containing the seeded medium was shaken on a shaking table (260 RPM, amplitude 10 cm) at 25° C. for 18–20 hours. After this 50 ml (1%) of the shaken culture was seeded into 5 liter medium with mark E-5 sterilized at 121° C. for 45 min in a 10 liter jar fermentor. Composition of E-5 medium was the following:

| | |
|---|---|
| glucose* | 50 g |
| glycerol | 50 g |
| soy-bean meal | 100 g |
| corn steep liquor | 15 g |
| sodium chloride | 25 g |
| calcium carbonate | 25 g |
| sunflower oil | 10 g | diluted up to 5 liters with tap water. (*Glucose was sterilized in 50% solution for 30 min, and added into the medium together with the seeding material.) The pH of the medium was set to 7.0 before sterilization.

The cultivation was stirred and aerated for 50–60 hours. The temperature of the cultivation was 25° C., stirring rate was 500 RPM, airflow rate was 200 liters/hour. As an antifoaming agent, sunflower oil was used in minimal quantity (about 20–30 ml per fermentor).

The biosynthesis of the pseudomonic acid complex was started at hours 8–10 of the fermentation and the maximal antibiotic concentration was experienced at hours 55–60 hours of the culture.

Isolation of the pseudomonic acid A from the fermentation broth was carried out as follows: After finishing the fermentation, the 4.5 liter culture broth obtained was centrifuged, then the pH of the supernatant (4.06 liter) was adjusted to 4.5 with diluted (20%) sulfuric acid. The acidified liquor was then twice extracted by 2.03 liters ethyl acetate. The phases were separated and a sharp phase was prepared from the emulsive organic phase by centrifugation. The combined extract was evaporated in vacuum. The crude product obtained (2.45 g) was dissolved in a 25 ml mixture of chloroform-methanol-99.5% acetic acid (93:5:2), and the solution obtained was loaded on the column (height:diameter=28.5) prepared from 245 g Kieselgel 60 (particle size: 0.063–0.2 mm; Reanal) and with the above solvent mixture. Elution was carried out with the above solvent mixture. In the course of the elution 50 ml fractions were collected and the pseudomonic acid A content of the fractions was analyzed by thin layer chromatography using Kieselgel 60 (DC-Alufolien: 105554, Merck) adsorbent and chloroform-methanol-99.5% acetic acid (90:8:2) developing solvent mixture. Fractions 34–50 eluted from the Kieselgel 60 column contained pseudomonic acid A. These fractions were combined (850 ml) and meanwhile cooling 280 ml water was added to the solution obtained. After this the pH of the solution mixture was adjusted to 4.5 with 1N aqueous sodium hydroxide solution. The organic solution was separated from the water phase, then the water phase was extracted again by 280 ml chloroform. The combined extract was evaporated in vacuum, thus pure pseudomonic acid A could be obtained.

The column chromatographic fractions 14–15 contained pseudomonic acid C, while fraction 54 contained pseudomonic acid B, from the minor components could be recovered in pure form by the above written procedure.

The spectroscopic characterization of the isolated pseudomonic acid components was described using the numbering system of structural formula (I), shown above.

Spectroscopic Characterization of the Pseudomonic Acid A

Ultraviolet spectrum (10 μg/ml, in 95% ethanol solution): $\lambda_{max}$=222 nm $E_{1\ cm}^{1\%}$=303.6

Infrared spectrum (KBr): $\nu_{OH}$ 3483 and 3306, $\nu_{c=o}$ 1728 (COOCH$_2$), 1720 (COOH) cm$^{-1}$ $^1$H-NMR spectrum (CDCl$_3$, $\delta_{TMS}$ = 0):

| δ [ppm], (integral), multiplicity | Coupling constant (Hz) | Assignment |
|---|---|---|
| 5.75 (1H) q | $^4J_{2,15}$ = 1.1 | 2-H |
| 4.08 (2H)t | $^3J_{8',9'}$ = 6.4 | 9'-H$_2$ |
| 3.72–3.93 (4H)m |  | 5-H; 7-H; 13-H; 16-H$_a$ |
| 3.55 (1H) dd | $^2J_{16a,16b}$ = 11.8; $^3J_{16b,8}$ = 2.6 | 16-H$_b$ |
| 3.48 (1H)dd | $^3J_{5,6}$ = 8.4; $^3J_{6,7}$ = 3.2 | 6-H |
| 2.82 (1H)td | $^3J_{9,10}$ = 6.3; $^3J_{10,11}$ = 2.3 | 10-H |
| 2.74 (1H)dd | $^3J_{10,11}$ = 2.3; $^3J_{11,12}$ = 7.8 | 11-H |
| 2.60 (1H)dd | $^2J_{4a,4b}$ = 14.5; $^3J_{4a,5}$ = 2.7 | 4-H$_a$ |
| 2.28–2.36 (3H)m |  | 4-H$_b$; 2'-H$_2$ |
| 2.20 (3H)d | $^4J_{2,15}$ = 1.1 | 15-H$_3$ |
| 2.02 (1H)m |  | 8-H |
| 1.61–1.76 (6H)m |  | 9-H$_2$; 3'-H$_2$; 8'-H$_2$ |
| 1.33–1.43 (9H)m |  | 12-H; 4'-H$_2$; 5'-H$_2$; 6'-H$_2$; 7'-H$_2$ |
| 1.22 (3H)d | $^3J_{13,14}$ = 6.4 | 14-H$_3$ |
| 0.94 (3H)d | $^3J_{12,17}$ = 7.0 | 17-H$_3$ |

$^{13}$C-NMR spectrum (CDCl$_3$ solution, $\delta_{TMS}$ = 0):

| δ [ppm] | Assignment | δ [ppm] | Assignment |
|---|---|---|---|
| 177.8 s | C-1' | 42.7t,d | C-4, C-12 |
| 166.9s | C-1 | 39.4d | C-8 |
| 156.0s | C-3 | 33.9t,t | C-9, C-2' |
| 117.7d | C-2 | 31.6t | C-4'* |
| 74.9d | C-5 | 28.9t | C-5'* |
| 71.4d | C-13 | 28.8t | C-6'* |
| 70.4d | C-7 | 28.5t | C-8'* |
| 69.0d | C-6 | 25.9t | C-7' |
| 65.3t | C-16 | 24.6t | C-3' |
| 63.9t | C-9' | 20.8q | C-14 |
| 61.3d | C-11 | 19.1q | C-15 |
| 55.6d | C-10 | 12.7q | C-17 |
| *interchangeable assignments |

Chemical ionization (CI) mass spectrum:
Characteristic spectral data:

| m/z | R.I. (%) | Assignment |
|---|---|---|
| 501 | 100 | [M + H]$^+$ |
| 327 | 45 | [M + H—HO/CH$_2$/$_8$COOH]$^+$ |
| 309 | 16 | [m/z 327-H$_2$O]$^+$ |
| 227 | 33 | [C$_{12}$H$_{19}$O$_4$]$^+$ |

Spectroscopic Characterization of the Pseudomonic Acid B

Ultraviolet spectrum (10 μg/ml, in 95% ethanol solution): $\lambda_{max}$=222 nm $E_{1\ cm}^{1\%}$=280

Infrared spectrum (film): $\nu_{OH}$3418, $\nu_{c=o}$1713 (COOCH$_2$, COOH)cm$^{-1}$ $^1$H-NMR spectrum (CDCl$_3$, $\delta_{TMS}$ = 0):

| δ [ppm], (integral), multiplicity | Coupling constant (Hz) | Assignment |
|---|---|---|
| 5.68 (1H) s |  | 2-H |
| 4.02 (2H)t | $^3J_{8',9'}$ = 6.6 | 9'-H$_2$ |
| 3.7 (2H)m |  | 7-H,13-H |
| 3.55 (1H)td | $^3J_{4a,5}$ = $^3J_{5,6}$ = 9.3; $^3J_{4b,5}$ = 1.8 | 5-H |
| 3.41 (2H)dd | $^2J_{16a,16b}$ = 11.0 | 16-H$_2$ |
| 3.24 (1H)dd | $^3J_{5,6}$ = 9.3; $^3J_{6,7}$ = 2.8 | 6-H |
| 2.92 (1H)td | $^3J_{9,10}$ = 5.6; $^3J_{10,11}$ = 2.0 | 10-H |
| 2.69 (1H)dd | $^3J_{10,11}$ = 2.0; $^3J_{11,12}$ = 7.2 | 11-H |
| 2.62(1H)dd | $^2J_{4a,4b}$ = 14.5; $^3J_{4a,5}$ = 1.9 | 4-H$_a$ |
| 2.20 (2H)t | $^3J_{2',3'}$ = 7.4 | 2'-H$_2$ |
| 2.14 (3H)br.s |  | 15-H$_3$ |
| 2.10 (1H)dd | $^2J_{4a,4b}$ = 14.5; $^3J_{4b,5}$ = 9.3 | 4-H$_b$ |
| 1.85 (1H)dd | $^2J_{9a,9b}$ = 14.3; $^3J_{9a,10}$ = 5.3 | 9-H$_a$ |
| 1.20–1.68 (14H)m |  | 9-H$_b$; 12-H; 3'-H$_2$; 4'-H$_2$; 5'-H$_2$; 6'-H$_2$; 7'-H$_2$; 8'-H$_2$ |
| 1.14(3H)d | $^3J_{13,14}$ = 6.4 | 14-H$_3$ |
| 0.88 (3H)d | $^3J_{12,17}$ = 7.1 | 17-H$_3$ |

Chemical ionization (CI) mass spectrum:
Characteristic spectral data:

| m/z | RI (%) | Assignment |
|---|---|---|
| 517 | 100 | [M + H]$^+$ |
| 343 | 70 | [M + H—HO/CH$_2$/$_8$COOH]$^+$ |

Spectroscopic Characterization of the Pseudomonic Acid C

Ultraviolet spectrum (10 μg/ml, in 95% ethanol solution): $\lambda_{max}$=222 nm $E_{1\ cm}^{1\%}$=307.

Infrared spectrum (film): $\nu_{OH}$3455, $\nu_{c=o}$1713 (COOCH$_2$, COOH)cm$^{-1}$ $^1$H-NMR spectrum (CDCl$_3$, $\delta_{TMS}$ = 0):

| δ [ppm] (integral), multiplicity | Coupling constant (Hz) | Assignment |
|---|---|---|
| 5.69 (1H)s |  | 2-H |
| 5.25–5.50 (2H)m |  | 10-H; 11-H |
| 4.00 (2H)t | $^3J_{8',9'}$ = 6.5 | 9'-H$_2$ |
| 3.88 (1H)dd | $^3J_{6,7}$ = $^3J_{7,8}$ = 3.0 | 7-H |
| 3.78 (1H)dd | $^2J_{16a,16b}$ = 11.8; $^3J_{16a,8}$ = 2.6 | 16-H$_a$ |
| 3.68 (1H)dd | $^3J_{4b,5}$ = 2.5; $^3J_{5,6}$ = 9.0 | 5-H |
| 3.55 (1H)qd | $^3J_{12,13}$ = $^3J_{13,14}$ = 6.3 | 13-H |
| 3.49 (1H)dd | $^2J_{16a,16b}$ = 11.8; $^3J_{16b,8}$ = 2.0 | 16-H$_b$ |
| 3.41 (1H)dd | $^3J_{5,6}$ = 9.0; $^3J_{6,7}$ = 3.0 | 6-H |
| 2.58 (1H)dd | $^2J_{4a,4b}$ = 13.8; $^3J_{4a,5}$ = 2.5 | 4-H$_a$ |
| 2.20 (2H)t | $^3J_{2',3'}$ = 7.4 | 2'-H$_2$ |
| 2.00–2.30 (4H)m |  | 4-H$_b$; 9-H$_2$;12-H |
| 2.10 (3H)m |  | 15-H$_3$ |
| 1.78 (1H)m |  | 8-H |
| 1.45–1.65 (4H)m |  | 3'-H$_2$; 8'-H$_2$ |

-continued

| Infrared spectrum (film): $\nu_{OH}$3455, $\nu_{c=o}$1713 (COOCH$_2$, COOH)cm$^{-1}$ | | |
|---|---|---|
| $^1$H-NMR spectrum (CDCl$_3$, $\delta_{TMS}$ = 0): | | |
| δ [ppm] (integral), multiplicity | Coupling constant (Hz) | Assignment |
| 1.15–1.35 (8H)m | | 4'-H$_2$; 5'-H$_2$; 6'-H$_2$, 7'-H$_2$ |
| 1.08 (3H)d | $^3J_{13,14}$ = 6.3 | 14-H$_3$ |
| 0.92 (3H)d | $^3J_{12,17}$ = 6.8 | 17-H$_3$ |

Chemical ionization (CI) mass spectrum:

Characteristic spectral data:

| m/z | R.I. (%) | Assignment |
|---|---|---|
| 485 | 30 | [M + H]$^+$ |
| 287 | 60 | [M + H—HO/CH$_2$/$_8$COOH]$^+$ |

Although certain presently preferred embodiments of the invention have been described herein, it will be apparent to those skilled in the art to which the invention pertains that variations and modifications of the describe embodiment may be made without departing from the spirit and scope of the invention. Accordingly, it is intended that the invention be limited only to the extent required by the appended claims and the applicable rules of the law.

We claim:

1. A biologically pure culture of Pseudomonas sp. bacterium strain No. 19/26 deposited under accession No. NCAIM(P)B 001235 in the National Collection of Agricultural and Industrial Microorganisms, Budapest, Hungary.

* * * * *